(12) United States Patent
Chin

(10) Patent No.: US 7,875,060 B2
(45) Date of Patent: Jan. 25, 2011

(54) MULTI-AXIAL SCREW WITH A SPHERICAL LANDING

(75) Inventor: Kingsley R. Chin, Philadelphia, PA (US)

(73) Assignee: Spinefrontier, LLS, Philadelphia, PA (US)

( * ) Notice: Subject to any disclaimer, the term of this patent is extended or adjusted under 35 U.S.C. 154(b) by 377 days.

(21) Appl. No.: 11/156,435

(22) Filed: Jun. 20, 2005

(65) Prior Publication Data

US 2005/0234454 A1   Oct. 20, 2005

Related U.S. Application Data

(63) Continuation-in-part of application No. 10/669,927, filed on Sep. 24, 2003.

(60) Provisional application No. 60/582,893, filed on Jun. 25, 2004.

(51) Int. Cl.
*A61F 5/00* (2006.01)

(52) U.S. Cl. ........................ 606/267; 606/266

(58) Field of Classification Search .............. 606/61, 606/278, 270–272, 280, 286–290, 291–295, 606/300–302, 305, 319, 250, 260, 264–274, 606/276, 70, 71, 328; 411/340, 346, 549, 411/550, 554, 356, 359, 365, 380, 393, 403; 81/461

See application file for complete search history.

(56) References Cited

U.S. PATENT DOCUMENTS

| 5,591,166 | A  | * | 1/1997 | Bernhardt et al. | 606/266 |
| 5,725,528 | A  | * | 3/1998 | Errico et al. | 606/266 |
| 5,885,286 | A  | * | 3/1999 | Sherman et al. | 606/270 |
| 6,106,526 | A  | * | 8/2000 | Harms et al. | 606/278 |
| 6,267,765 | B1 | * | 7/2001 | Taylor et al. | 606/61 |
| 6,290,703 | B1 | * | 9/2001 | Ganem | 606/250 |
| 6,733,502 | B2 | * | 5/2004 | Altarac et al. | 606/61 |
| 7,335,201 | B2 | * | 2/2008 | Doubler et al. | 606/264 |
| 2003/0073996 | A1 | * | 4/2003 | Doubler et al. | 606/61 |
| 2003/0153911 | A1 | * | 8/2003 | Shluzas | 606/61 |
| 2003/0216735 | A1 | * | 11/2003 | Altarac et al. | 606/61 |

OTHER PUBLICATIONS http://wordnet.princeton.edu/perl/webwn?s=plate.*

* cited by examiner

*Primary Examiner*—Eduardo C Robert
*Assistant Examiner*—Tara R Carter
(74) *Attorney, Agent, or Firm*—AKC Patents LLC; Aliki K. Collins

(57) ABSTRACT

A multi-axial screw assembly with a spherical landing surface is disclosed. The multi-axial screw assembly 100 includes a bone anchor 150, a head 130 with a spherical outer surface and an extension member 160 extending from the top of the head 130. The multi-axial screw is designed to attach a planar or semispherical end member of a plate to a vertebra. The plate is part of a spine fixation or stabilization assembly. The multi-axial screw provides multi-axial pivoting of the screw relative to the plate.

24 Claims, 8 Drawing Sheets

MULTI-AXIAL SCREW WITH A SPHERICAL LANDING

CROSS REFERENCE TO RELATED CO-PENDING APPLICATIONS

This application claims the benefit of U.S. provisional application Ser. No. 60/582,893 filed on Jun. 25, 2004 and entitled MULTI-AXIAL SCREW WITH A SPHERICAL LANDING which is commonly assigned and the contents of which are expressly incorporated herein by reference.

This application is also a continuation in part of U.S. application Ser. No. 10/669,927 filed on Sep. 24, 2003 and entitled APPARATUS AND METHOD FOR CONNECTING SPINAL VERTEBRAE the contents of which are expressly incorporated herein by reference.

FIELD OF THE INVENTION

The present invention relates to a multi-axial screw, and more particularly to a multi-axial screw with a spherical landing surface for receiving a plate stabilization element.

BACKGROUND OF THE INVENTION

Patents U.S. Pat. Nos. 6,626,909 and 6,669,729, the entire contents of which are expressly incorporated herein by reference describe spine fixation assemblies that utilize plates as connecting and stabilization elements. Plates are secured to vertebral bones via screws. The screws presented in these two patents are capable of pivoting around a fixed axis of the stabilization plates to achieve variable angular positions relative to the plates. This limited range of relative angular positioning is acceptable for many spinal pathologies. However, in some cases it is preferred to have screws that provide multi-axial pivoting relative to the stabilization plates.

SUMMARY OF THE INVENTION

In general, in one aspect, the invention features a bone anchor assembly for engaging an elongated plate element including a bone engaging anchor, a spherical member, a head, and a locking member. The bone engaging anchor has a body portion configured to engage a bone, a spherical top end and a sharp bottom end. The spherical member is configured to grip and lock the spherical top of the bone engaging anchor. The head has a spherical outer surface for receiving a semispherical end member of the elongated plate element and is configured to sit upon the spherical member. The locking member is used for securing the semispherical end member to the head and the head to the spherical member.

Implementations of this aspect of the invention may include one or more of the following features. The spherical top of the bone engaging anchor comprises a rough outer surface and a bore designed to receive a tool for screwing the bone engaging anchor into a bone. The rough outer surface of the spherical top comprises elements including serrations, knurling or horizontal elevations. The spherical member comprises a circular cross-section or a c-shaped cross-section. The spherical member comprises a smooth outer surface, an opening configured to receive the tool, and a rough inner surface configured to grip and lock with the rough outer surface of the spherical top of the bone engaging anchor. The rough inner surface of the spherical member comprises elements including serrations, knurling or horizontal elevations and these elements are configured to cooperate with the corresponding elements of the outer surface of the spherical top. The head comprises an opening configured to receive the locking member, and a spherical inner surface configured to be interference fitted with the spherical outer surface of the spherical member. The head opening comprises inner threads configured to cooperate and engage with outer threads of the locking member thereby securing the head to the spherical member. The bone anchor assembly may further include a removable extension member configured to connect to the locking member. The locking member comprises a cylindrical body having threads on its outer surface and a bore on its top end for receiving an appendage of the removal extension member. The semispherical end member of the elongated plate element comprises an opening for receiving the locking member. The opening of the elongated plate element comprises inner threads adapted to cooperate with the threads of the locking member. The bone anchor assembly may further include a retention nut adapted to be threaded around outer threads of the removable extension member or the threads of the locking member. The extension member is an integral part of the locking member and is designed to be broken off or otherwise manually removed.

In general, in another aspect, the invention features a bone anchor assembly for engaging an elongated plate element including a bone engaging anchor, a spherical member, a crown, and a locking member. The bone engaging anchor has a body portion configured to engage a bone, a sharp bottom end and a top member. The top member comprises an upper opening portion extending into the center of the top member and a spherical head extending from the bottom of the upper opening portion. The top member further comprises a spherical outer surface for receiving a semispherical end member of the elongated plate member. The spherical member is configured to grip and lock the spherical head of the bone engaging anchor. The crown has a spherical inner surface and a cylindrical top and is configured to sit upon the spherical member. The locking member is used for securing the crown to the spherical member.

Implementations of this aspect of the invention may include one or more of the following features. The spherical head of the bone engaging anchor comprises a rough outer surface and a bore designed to receive a tool for screwing the bone engaging anchor into a bone. The rough outer surface of the spherical head comprises elements including serrations, knurling or horizontal elevations. The spherical member comprises a circular cross-section or a c-shaped cross-section. The spherical member comprises a smooth outer surface, an opening configured to receive the tool, and a rough inner surface configured to grip and lock with the rough outer surface of the spherical head of the bone engaging anchor. The rough inner surface of the spherical member comprises elements including serrations, knurling or horizontal elevations and these elements are configured to cooperate with the corresponding elements of the outer surface of the spherical head. The crown comprises an opening configured to receive the locking member, and a spherical inner surface configured to be interference fitted with the spherical outer surface of the spherical member. The crown opening comprises inner threads configured to cooperate and engage with outer threads of the locking member thereby securing the crown to the spherical member. The semispherical end member of the elongated plate element comprises an opening for receiving the locking member. The opening of the elongated plate element comprises inner threads adapted to cooperate with outer threads of the crown.

BRIEF DESCRIPTION OF THE DRAWINGS

Referring to the figures, wherein like numerals represent like parts throughout the several views.

DETAILED DESCRIPTION OF THE INVENTION

The invention provides a multi-axial screw with a spherical landing surface for receiving a plate stabilization element.

Figure 1:
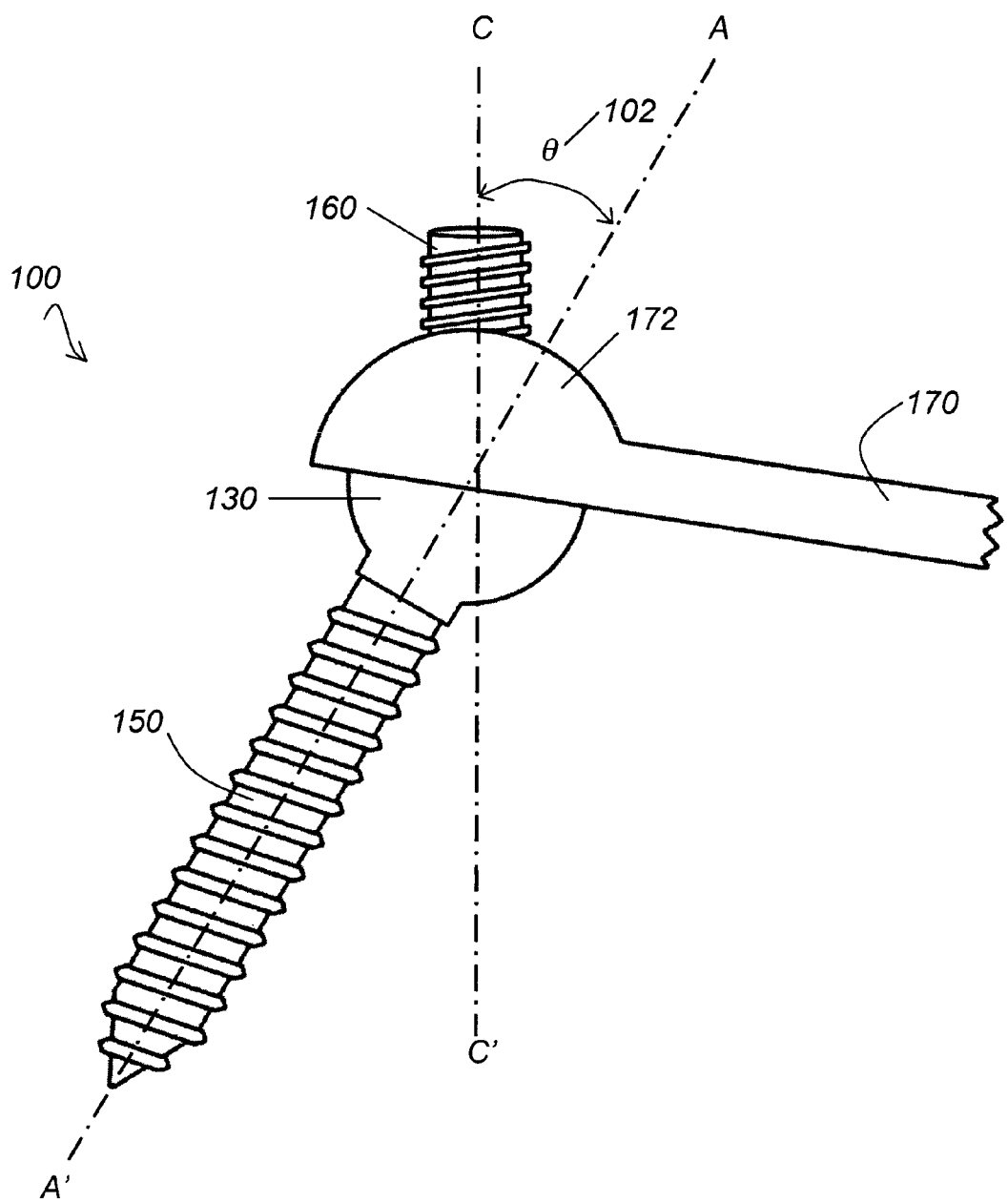
FIG. 1 is a side elevational view of a multi-axial screw assembly with a spherical landing surface.
Figure 2A:
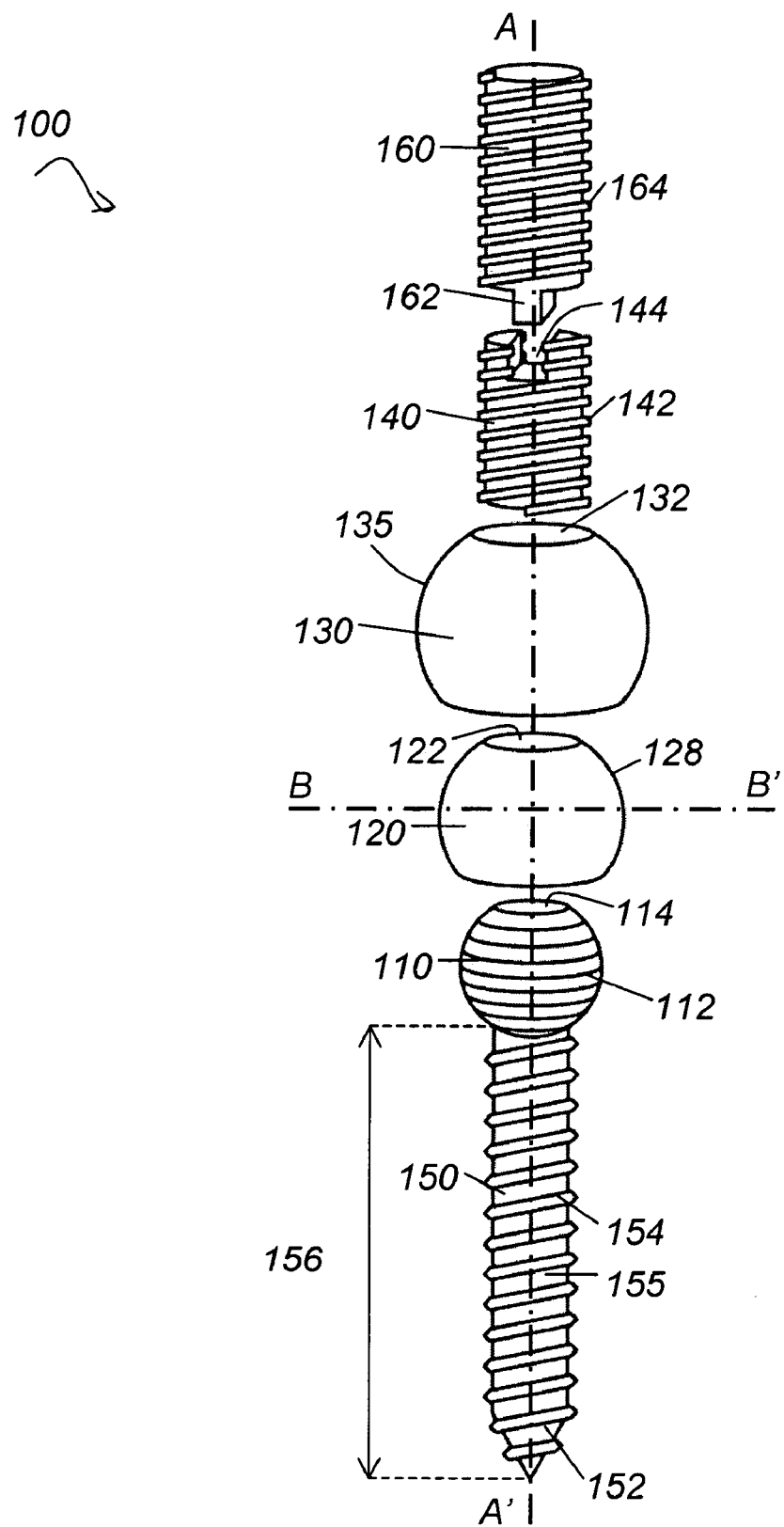
FIG. 2A is an exploded view of the multi-axial screw embodiment of FIG. 1.
Figure 2B:
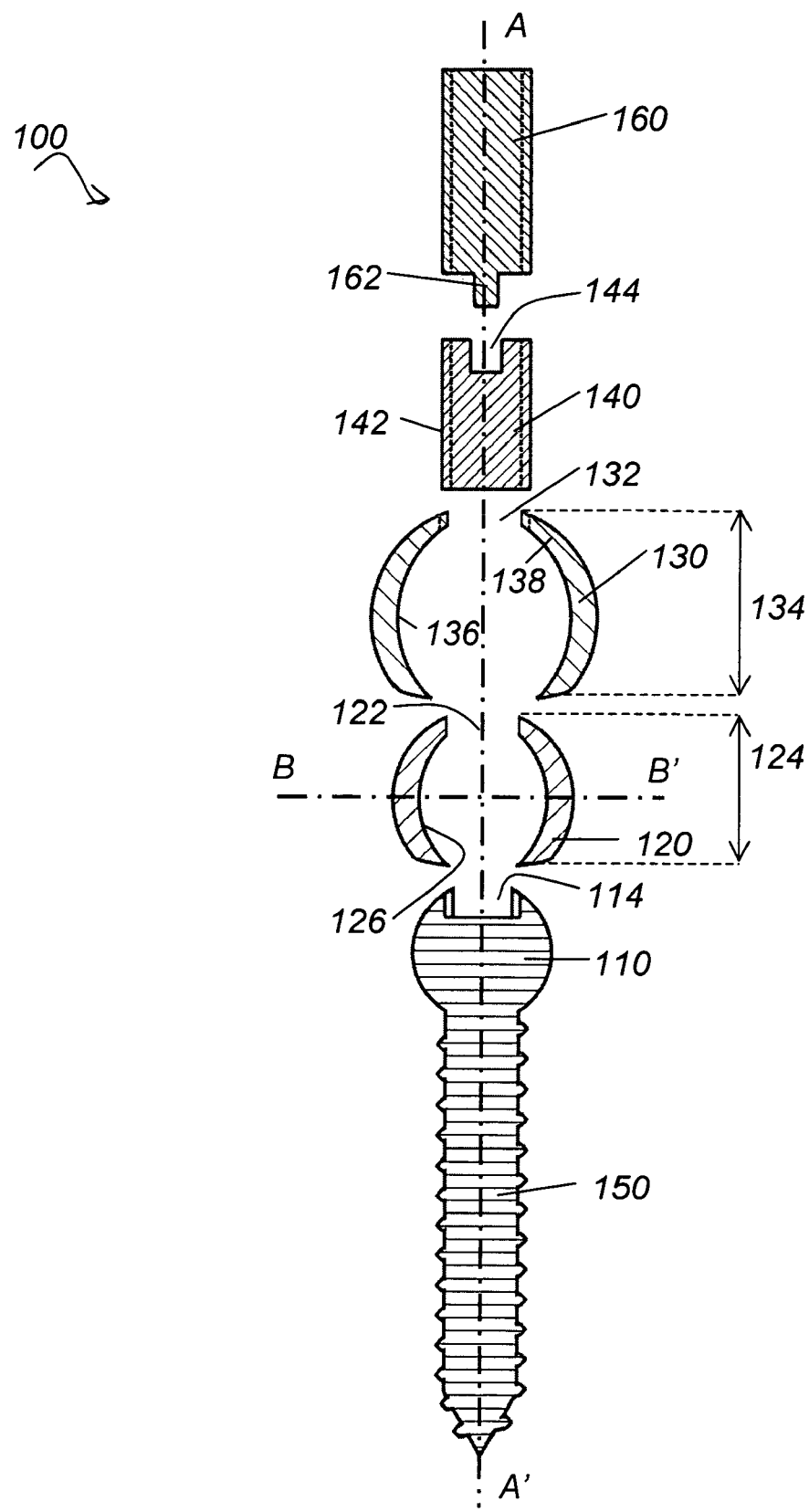
FIG. 2B is an exploded cross-sectional view of the multi-axial screw embodiment of FIG. 1.
Figure 2C:
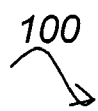
FIG. 2C is cross-sectional view of one embodiment of the spherical member 120.
Figure 2C:
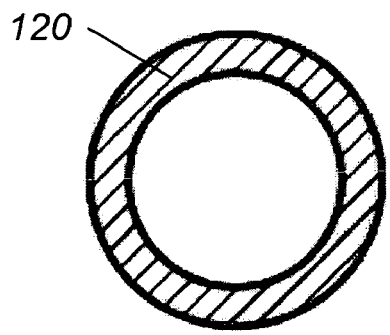
Figure 2D:
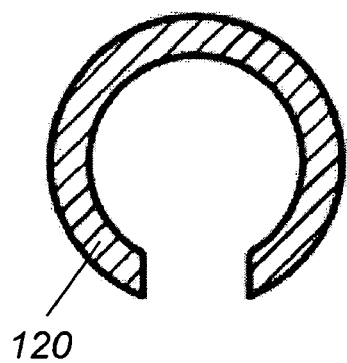
FIG. 2D is a cross-sectional view of another embodiment of the spherical member 120.
Figure 3:
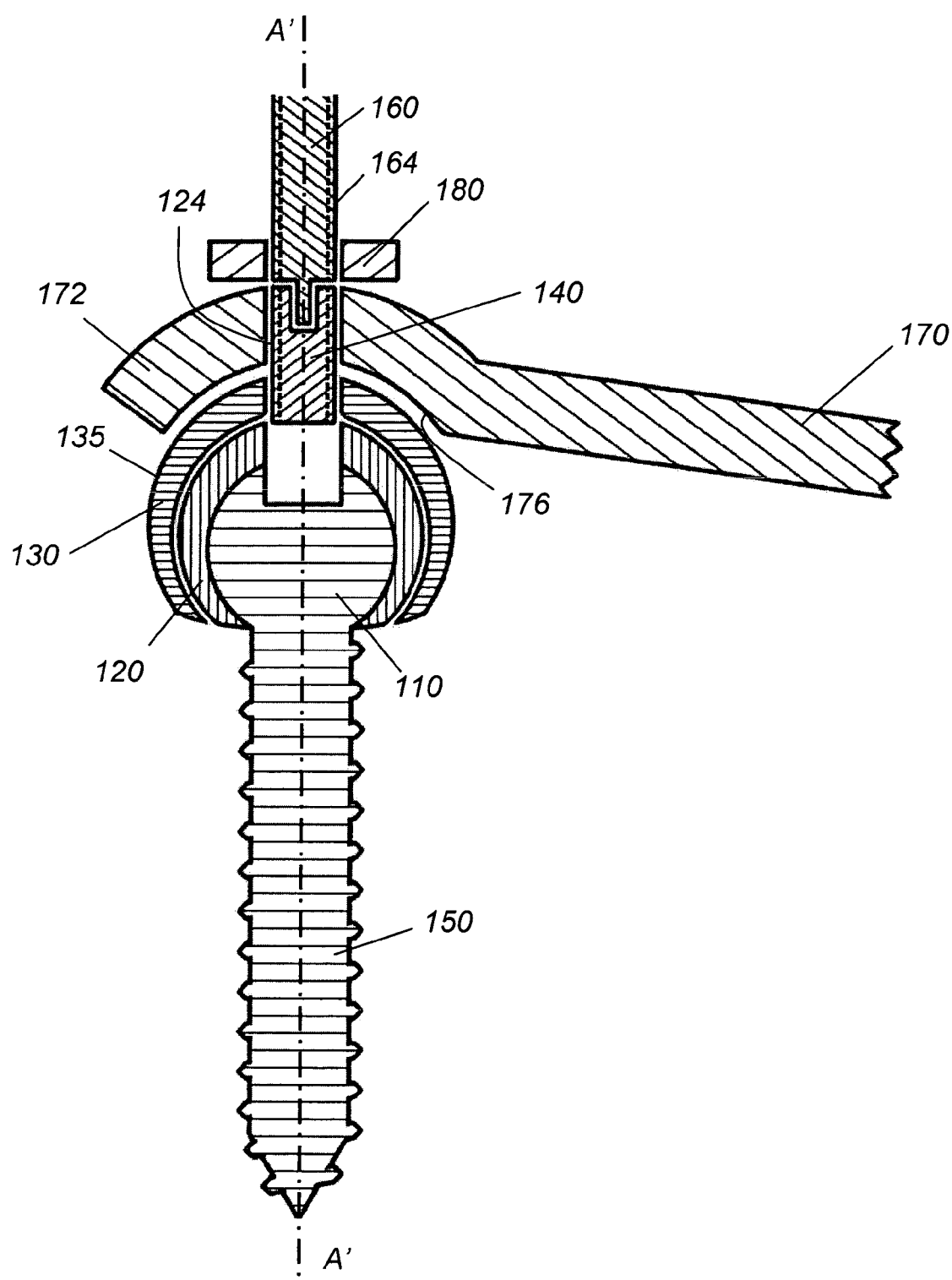
FIG. 3 is a cross-sectional view of the multi-axial screw assembly of FIG. 1 with an attached elongated plate.

Referring to FIG. 1, a multi-axial screw 100 assembly includes a bone anchor 150, a head 130 with a spherical outer surface and an extension member 160. The multi-axial screw 100 is designed to attach an elongated plate 170 with a semispherical end member 172 to a vertebral bone or any other bone. Referring to FIG. 2A and FIG. 2B, the bone anchor 150 includes a body 155 with outer threads 154 and terminates in a spherical top end 110 and a sharp bottom end 152. The spherical top end 110 has a rough outer surface 112 and a bore 114 designed to receive a tool (not shown) for screwing the bone anchor 150 into the bone. In other embodiments the outer surface of the spherical top end 110 includes serrations, knurling or horizontal elevations. The rough outer surface 112, the serrations, knurling or horizontal elevations provide a good gripping surface. On top of the spherical top end 110 sits a hollow spherical member 120. Spherical member 120 has a circular cross-section along the BB' axis, shown in FIG. 2C. In other embodiments spherical member 120 has a c-shaped cross-section along the BB' axis, shown in FIG. 2D. Spherical member 120 has an opening 122 and a spherical inner surface 126 that is configured to accommodate and grip the rough outer surface 112 of the spherical top end 110. Inner surface 126 can be rough or have serrations, horizontal elevations or knurling that can cooperate with the roughness, serrations, horizontal elevations or knurling of the outer surface 112 of the spherical top end 110. Opening 122 is provided so that a tool can be inserted through the opening 122 to reach the bore 114 of the spherical top end 110 for screwing the bone anchor 150 into the bone. The radius of the spherical member 120 is slightly larger that the radius of the spherical top end 110 and slightly smaller than the radius of the head 130 so that it can be interference fitted between them. Head 130 has a spherical outer surface 135 configured to provide a spherical landing surface for the end member 172 of the elongated plate 170, shown in FIG. 3 and FIG. 1. Head 130 has an opening 132 that allows the above mentioned tool to reach the bore 114 of the spherical top end 110 for screwing the bone anchor 150 into the bone. Head 130 sits on top of the spherical member 120 and the inner surface 136 of the head 130 is interference fitted with the outer surface 128 of the spherical member 120. The top portion of opening 132 has inner threads 138 for receiving a locking member 140. Locking member 140 has a cylindrical shape and outer threads 142 that cooperate with the inner threads 138 of the head 130 thereby tightening head 130 to spherical member 120 and to spherical top end 110. Locking member 140 has a bore 144 on its top end for receiving a cylindrical appendage 162 of the removable extension member 160. This configuration allows the extension member 160 to be positioned so that it always points in the vertical direction CC' while the screw axis AA' is oriented at an angle 102 away from the vertical CC' axis, shown in FIG. 1. Referring to FIG. 3, semispherical end member 172 of the elongate plate 170 has a through opening 174 that allows it to be placed over the locking member 140. The bottom surface 176 of the semispherical end member 172 sits on top of the spherical outer surface 135 of head 130. End member 172 can be rotated around axis AA' while the extension member 160 always points in the vertical CC' axis. Opening 174 may also have inner threads that cooperate with the outer threads 142 of the locking member 140. A retention nut 180 is threaded around outer threads 164 of the extension member 160 and the outer threads 142 of the locking member 140 in order to tighten the end member 172 to the spherical outer surface 135 of the head 130. In one example, the length 156 of the threaded body 155 is in the range of 14 mm to 30 mm for screws used in cervical vertebrae and 35 mm to 50 mm for screws used in lumbar vertebrae. In other examples, length 156 is in the range of 10 mm to 60 mm. In one example, multi-axial screw assembly 100 is made of titanium metal. In this configuration the head 130 may be rotated at any angle 102 relative to the screw axis AA' and tighten down to the top end 110 via the locking member 140. Preferably, head 130 is rotated so that the extension member 160 points in the vertical direction CC' while the bone anchor 150 is placed at any other angle 102 relative to the vertical axis CC'. In this example, bone anchor 150 is a screw. In other embodiments bone anchor 150 may be a hook. Furthermore, in other embodiments extension member 160 is an integral member of the locking member 140 and it can be broken off after the multi-axial screw assembly 100 is properly oriented and secured to the bone.

Figure 4:
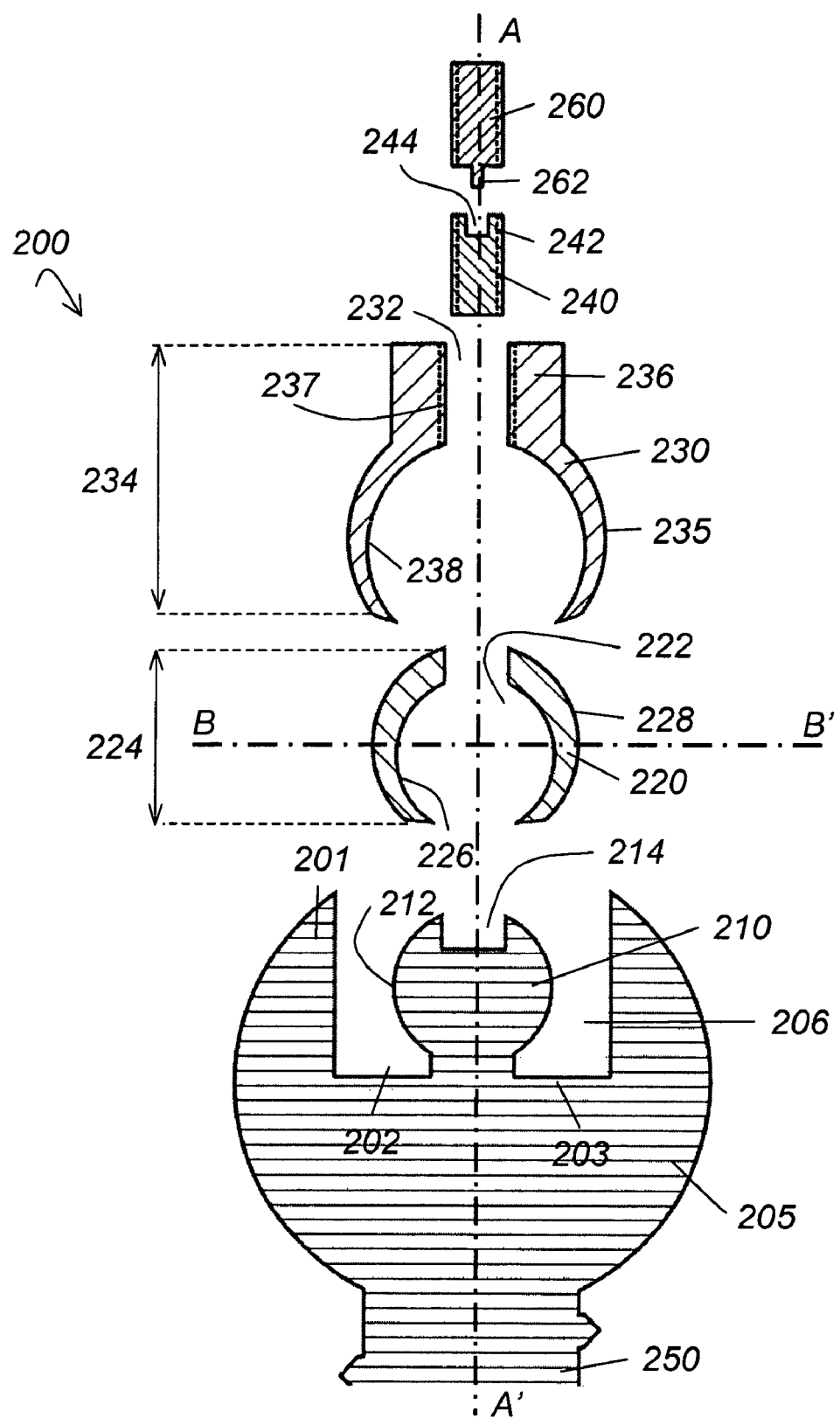
FIG. 4 is an exploded cross-sectional side view of another embodiment of a multi-axial screw with a spherical landing surface.
Figure 5:
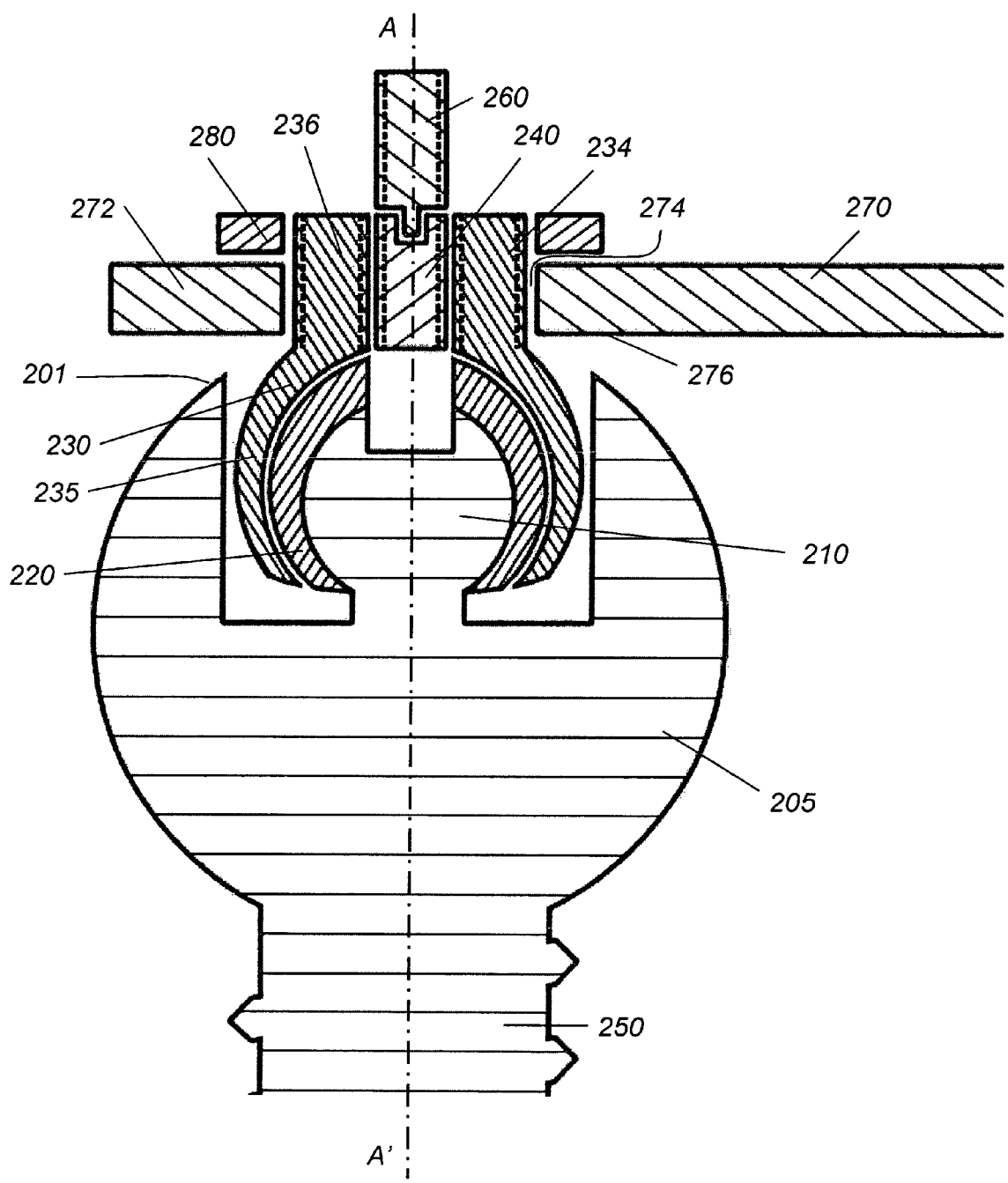
FIG. 5 is a cross-sectional view of the multi-axial screw assembly of FIG. 4 with an attached elongated plate.

Referring to FIG. 4 and FIG. 5, in another embodiment of a multi-axial screw assembly with a spherical landing surface, assembly 200 includes a bone anchor 250 having a spherical head 205. Spherical head 205 has a cylindrical bore opening 206 extending from the top surface 201 of spherical head 205 halfway into the center 202 of the spherical head 205. From the bottom 203 of the bore opening 206 extends a spherical top end 210. Spherical top end 210 has a rough outer surface 212 and a top bore opening 214 for receiving a tool (not shown) for screwing the bone anchor 250 into a bone. In other embodiments the outer surface 212 of the spherical top end 210 includes serrations, knurling or horizontal elevations. The rough outer surface 212, the serrations, knurling or horizontal elevations provide a good gripping surface. On top of the spherical top end 210 sits a spherical member 220. Spherical member 220 has a circular cross-section along the BB' axis, as shown in FIG. 2C. In other embodiments spherical member 220 has a c-shaped cross-section along the BB' axis, as shown in FIG. 2D. Spherical member 220 has an opening 222 and a spherical inner surface 226 that is configured to accommodate and grip the rough outer surface 212 of the spherical top end 210. Inner surface 226 can be rough or have serrations, horizontal elevations or knurling that can cooperate with the roughness, serrations, horizontal elevations or knurling of the outer surface 212 of the spherical top end 210. Opening 222 is provided so that a tool can be inserted through the opening 222 to reach the bore 214 of the spherical top end 210 for screwing the bone anchor 250 into the bone. The radius of the spherical member 220 is slightly larger that the radius of the spherical top end 210 and slightly smaller than the radius of crown 230 that sits on top of it so that it can be interference fitted between them. Crown 230 has a spherical outer surface 235 and a cylindrical extension 236. Crown 230 has an opening 232 that allows the above mentioned tool to reach the bore 214 of the spherical top end 210 for screwing the bone anchor 250 into the bone. Crown 230 sits on top of the spherical member 220 and the inner surface 238 of the crown 230 is interference fitted with the outer surface 228 of the spherical member 220. The top portion of opening 232 has inner threads 237 for receiving a locking member 240. Locking member 240 has a cylindrical shape and outer threads 242 that cooperate with the inner threads 237 of the crown 230 thereby tightening crown 230 to spherical member 220 and to spherical top end 210. Locking member 240 has a bore 244 on its top end for receiving a cylindrical appendage 262 of the removable extension member 260. This configuration allows the extension member 260 to always point in the vertical direction CC' while the screw axis AA' is oriented at an angle 102 away from the vertical CC' axis, as shown in FIG. 1.

Referring to FIG. 5, planar end member 272 of the elongate plate 270 has a through opening 274 that allows it to be placed over the cylindrical extension 236 of the crown 230. The bottom surface 276 of the semispherical end member 272 sits on top of the spherical outer surface 201 of spherical head 205. End member 272 can be rotated around axis AA' while the extension member 260 always points in the vertical CC' axis. Opening 274 may also have inner threads that cooperate with outer threads 239 of the cylindrical extension 236. A retention nut 280 is threaded around outer threads 239 of the cylindrical extension 236 in order to tighten the end member 272 to the spherical outer surface 201 of the spherical head 205. In this configuration crown 230 may be rotated at any angle 102 relative to the screw axis AA' and tighten down to the top end 210 via the locking member 240. Preferably, crown 230 is rotated so that the extension member 260 points in the vertical direction CC' while the bone anchor 250 is placed at any other angle 102 relative to the vertical axis CC'.

Figure 6:
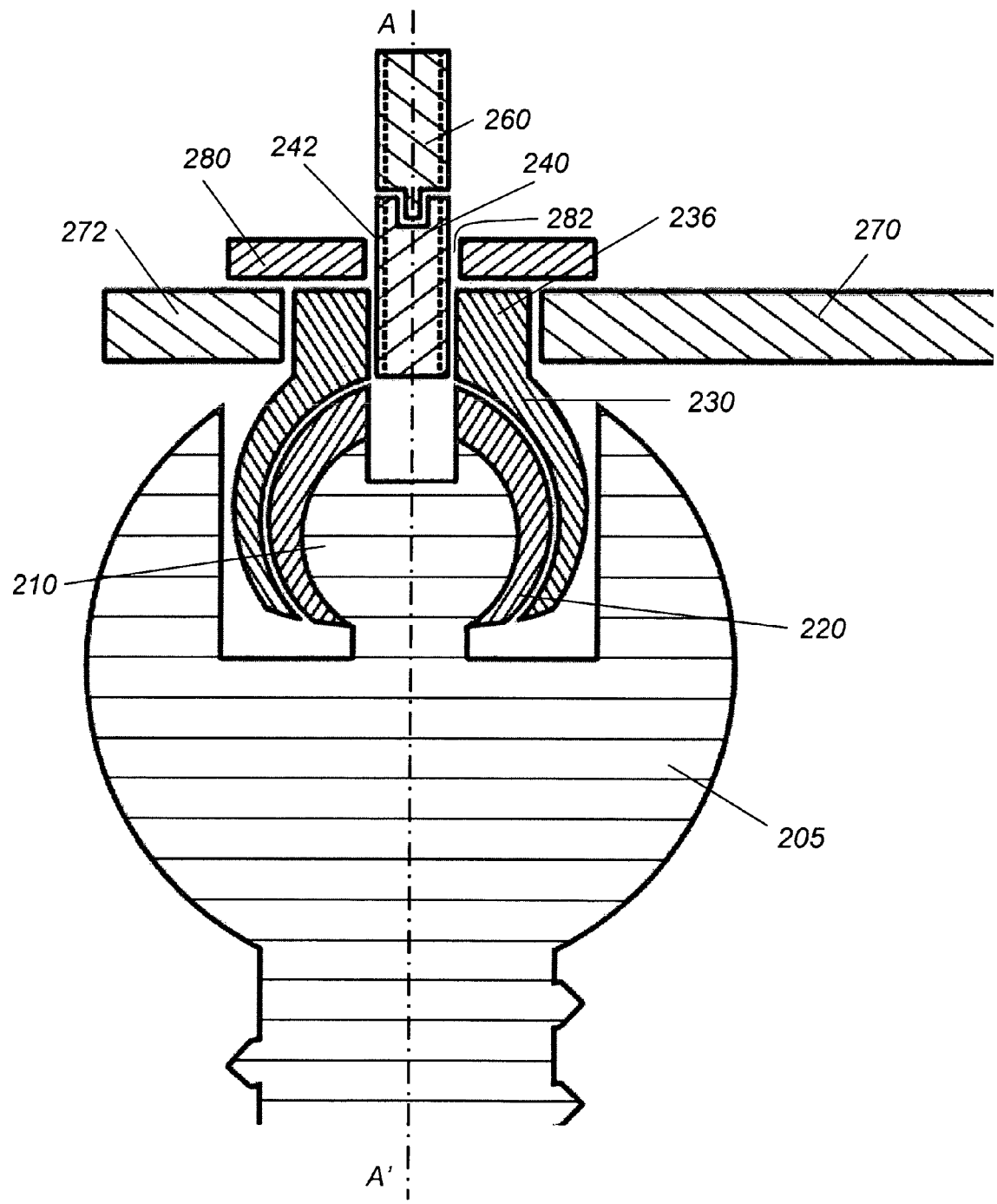
FIG. 6 is a cross-sectional view of another embodiment of the multi-axial screw assembly of FIG. 4 with an attached elongated plate.

In the embodiment of FIG. 6, the retention nut 280 is threaded around the locking member 240 and the inner threads 282 of nut 280 engage the outer threads 242 of the locking member 240. In another embodiment, nut 280 counter sinks with a crater-type groove in the elongated plate 270.

Several embodiments of the present invention have been described. Nevertheless, it will be understood that various modifications may be made without departing from the spirit and scope of the invention. Accordingly, other embodiments are within the scope of the following claims.

What is claimed is:

1. A bone anchor assembly for engaging an elongated plate element comprising an integrated semispherical end, said assembly comprising:
   a bone engaging anchor having a body portion configured to engage a bone, a spherical top end and a sharp bottom end;
   a hollow spherical component configured to grip an outer surface of said spherical top end and lock said spherical top of said bone engaging anchor;
   a head with a spherical outer surface configured to sit upon a spherical outer surface of said spherical component and configured to receive said semispherical end of said elongated plate element upon its spherical outer surface;
   a locking screw and wherein said head comprises an opening configured to receive said locking screw for securing said semispherical end to said head and said head to said spherical component; and
   wherein said locking screw comprises a breakable extension member that is designed to be broken off.

2. The bone anchor assembly of claim 1 wherein said spherical top of said bone engaging anchor comprises a rough outer surface and a bore designed to receive a tool for screwing said bone engaging anchor into a bone.

3. The bone anchor assembly of claim 2 wherein said rough outer surface of said spherical top comprises elements selected from a group consisting of serrations, knurling and horizontal elevations.

4. The bone anchor assembly of claim 3 wherein said spherical component comprises a smooth outer surface, an opening configured to receive said tool, and a rough inner surface configured to grip and lock with said rough outer surface of said spherical top of said bone engaging anchor.

5. The bone anchor assembly of claim 4 wherein said rough inner surface of said spherical component comprises elements selected from a group consisting of serrations, knurling and horizontal elevations and wherein said elements are configured to cooperate with the corresponding elements of said outer surface of said spherical top.

6. The bone anchor assembly of claim 1 wherein said spherical component comprises a circular cross-section.

7. The bone anchor assembly of claim 1 wherein said spherical component comprises a c-shaped cross-section.

8. The bone anchor assembly of claim 1 wherein said head comprises a spherical inner surface configured to be interference fitted with the spherical outer surface of said spherical component.

9. The bone anchor assembly of claim 8 wherein said head opening comprises inner threads configured to cooperate and engage with outer threads of said locking screw thereby securing said head to said spherical component.

10. The bone anchor assembly of claim 9 wherein said semispherical end of said elongated plate element comprises an opening for receiving said locking screw.

11. The bone anchor assembly of claim 10 wherein said opening of said elongated plate element comprises inner threads adapted to cooperate with said threads of said locking screw.

12. The bone anchor assembly of claim 11 further comprising a retention nut adapted to be threaded around outer threads of said removable extension member or said threads of said locking screw.

13. The bone anchor assembly of claim 1 wherein said locking screw comprises a cylindrical body having threads on its outer surface and a bore on its top end for receiving an appendage of said extension member.

14. A bone anchor assembly for engaging an elongated plate element comprising a semispherical end member, said assembly comprising:
   a bone engaging anchor having a body portion configured to engage a bone, a sharp bottom end and a first spherical head, wherein said first spherical head comprises an upper opening portion extending into the center of said first spherical head and a second spherical head extending from the bottom of said upper opening portion and wherein said first spherical head comprises a spherical outer surface for receiving said semispherical end of said elongated plate member upon said spherical outer surface;

a spherical component configured to grip and lock said second spherical head of said bone engaging anchor;

a crown with a spherical inner surface and a cylindrical top and configured to sit upon said spherical component; and a locking screw for securing said crown to said spherical component.

15. The bone anchor assembly of claim 14 wherein said second spherical head of said bone engaging anchor comprises a rough outer surface and a bore designed to receive a tool for screwing said bone engaging anchor into a bone.

16. The bone anchor assembly of claim 15 wherein said rough outer surface of said second spherical head comprises elements selected from a group consisting of serrations, knurling and horizontal elevations.

17. The bone anchor assembly of claim 16 wherein said spherical component comprises a smooth outer surface, an opening configured to receive said tool, and a rough inner surface configured to grip and lock with said rough outer surface of said second spherical head of said bone engaging anchor.

18. The bone anchor assembly of claim 17 wherein said rough inner surface of said spherical component comprises elements selected from a group consisting of serrations, knurling and horizontal elevations and wherein said elements are configured to cooperate with the corresponding elements of said outer surface of said spherical head.

19. The bone anchor assembly of claim 14 wherein said spherical component comprises a circular cross-section.

20. The bone anchor assembly of claim 14 wherein said spherical component comprises a c-shaped cross-section.

21. The bone anchor assembly of claim 14 wherein said crown comprises an opening configured to receive said locking screw, and a spherical inner surface configured to be interference fitted with the spherical outer surface of said spherical component.

22. The bone anchor assembly of claim 21 wherein said crown opening comprises inner threads configured to cooperate and engage with outer threads of said locking screw thereby securing said crown to said spherical component.

23. The bone anchor assembly of claim 14 wherein said semispherical end of said elongated plate element comprises an opening for receiving said locking screw.

24. The bone anchor assembly of claim 23 wherein said opening of said elongated plate element comprises inner threads adapted to cooperate with outer threads of said crown.

* * * * *